United States Patent [19]
Gordon et al.

[11] Patent Number: 5,899,381
[45] Date of Patent: May 4, 1999

[54] ELECTROCHEMICAL DEVICE FOR DELIVERY OF VOLATILE SUBSTANCES

[75] Inventors: John H. Gordon; Ashok V. Joshi, both of Salt Lake City; Giorgio di Palma, Draper, all of Utah

[73] Assignee: Ceramatec, Inc., Salt Lake City, Utah

[21] Appl. No.: 08/803,009

[22] Filed: Feb. 21, 1997

[51] Int. Cl.$^6$ ........................................... A61L 9/04
[52] U.S. Cl. .................. 239/6; 239/34; 239/57; 239/135; 239/309
[58] Field of Search ................... 239/6, 34, 44, 239/47, 51.5, 57, 135, 136, 145, 309, 322, 327, 329; 261/35

[56] References Cited

U.S. PATENT DOCUMENTS

| | | |
|---|---|---|
| D. 306,644 | 3/1990 | Luthy ........................................ D23/366 |
| D. 315,789 | 3/1991 | Muderlak . |
| 338,770 | 3/1886 | Otto . |
| 1,696,774 | 12/1928 | Martin . |
| 1,916,235 | 7/1933 | Ruben . |
| 2,680,449 | 6/1954 | Toulmin, Jr. . |
| 2,807,215 | 9/1957 | Hawxhurst . |
| 2,924,359 | 2/1960 | Beremand . |
| 2,979,897 | 4/1961 | Studhalter et al. . |
| 2,984,188 | 5/1961 | Tuckey et al. . |
| 3,115,280 | 12/1963 | Battista . |
| 3,430,731 | 3/1969 | Satzinger . |
| 3,602,214 | 8/1971 | Loadom . |
| 3,685,734 | 8/1972 | Paciorek et al. . |
| 3,842,939 | 10/1974 | Satzinger . |
| 3,877,989 | 4/1975 | Waldman et al. . |
| 3,894,538 | 7/1975 | Richter . |
| 3,990,848 | 11/1976 | Corris . |
| 4,023,648 | 5/1977 | Orlitzky et al. . |
| 4,111,655 | 9/1978 | Quincey . |
| 4,145,001 | 3/1979 | Weyenberg et al. . |
| 4,254,910 | 3/1981 | Martin . |
| 4,320,873 | 3/1982 | Martens, III et al. . |
| 4,571,485 | 2/1986 | Spector . |
| 4,629,604 | 12/1986 | Spector . |
| 4,671,386 | 6/1987 | Orlitzky . |
| 4,774,082 | 9/1988 | Flashinski et al. . |
| 4,849,606 | 7/1989 | Martens, III et al. . |
| 4,902,278 | 2/1990 | Maget et al. ........................... 604/132 |
| 4,968,456 | 11/1990 | Muderlak et al. . |
| 4,969,874 | 11/1990 | Michel et al. . |
| 5,007,529 | 4/1991 | Spector . |
| 5,068,099 | 11/1991 | Sramek . |
| 5,136,684 | 8/1992 | Lonker et al. . |
| 5,171,485 | 12/1992 | Ryan . |
| 5,242,111 | 9/1993 | Nakoneczny et al. . |
| 5,250,265 | 10/1993 | Kawaguchi et al. . |
| 5,273,690 | 12/1993 | McDowell . |
| 5,299,736 | 4/1994 | Greene . |
| 5,342,584 | 8/1994 | Fritz et al. . |
| 5,354,264 | 10/1994 | Bae et al. . |
| 5,361,522 | 11/1994 | Green . |
| 5,373,581 | 12/1994 | Smith . |
| 5,398,851 | 3/1995 | Sancoff et al. . |
| 5,399,404 | 3/1995 | Laughlin et al. . |
| 5,431,859 | 7/1995 | Tobin . |
| 5,437,410 | 8/1995 | Babasade . |
| 5,439,100 | 8/1995 | Gordon et al. . |
| 5,454,122 | 10/1995 | Bergeron . |
| 5,478,505 | 12/1995 | McElfresh et al. . |
| 5,593,552 | 1/1997 | Joshi et al. ............................. 204/228 |

*Primary Examiner*—Andres Kashnikow
*Assistant Examiner*—Lisa Ann Douglas
*Attorney, Agent, or Firm*—Factor and Shaftal

[57] ABSTRACT

An electrically controlled pump (20) for dispersing a volatile substance into a local environment includes an enclosure defining a volume, a moveable member (52) separating the enclosure into first (54) and second (56) chambers (the second chamber containing non-solid composition which includes a volatile substance), an electrochemical cell (48) for generating gas. The electrochemical cell is associated with the enclosure, and is in fluid communication with the first chamber. A port preferably communicates the second chamber with a medium for dispersing the volatile substance into the local environment. Also, a case (58) may encase the pump and hold it in an upright position with respect to a surface upon which the case is positioned.

24 Claims, 3 Drawing Sheets

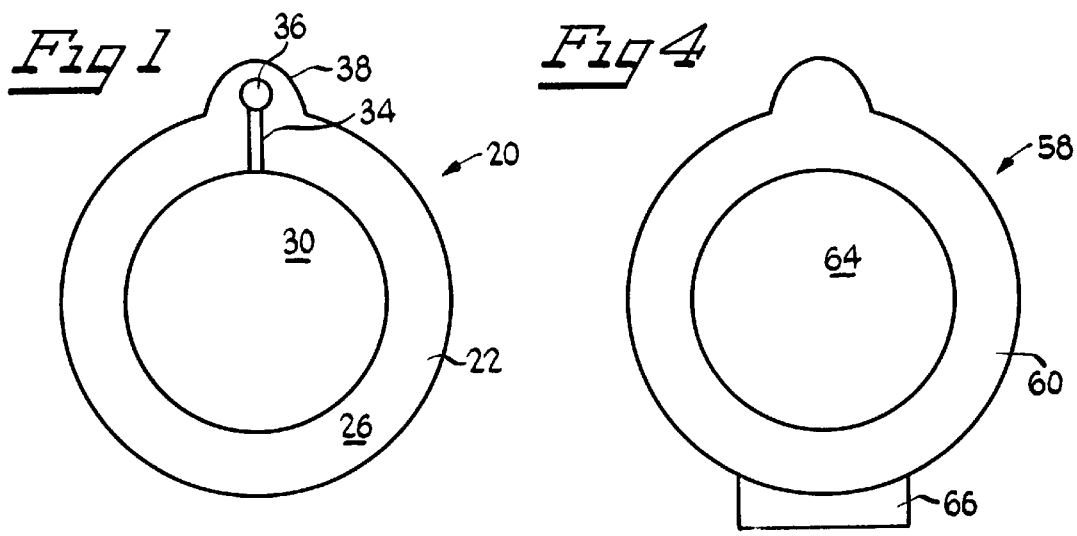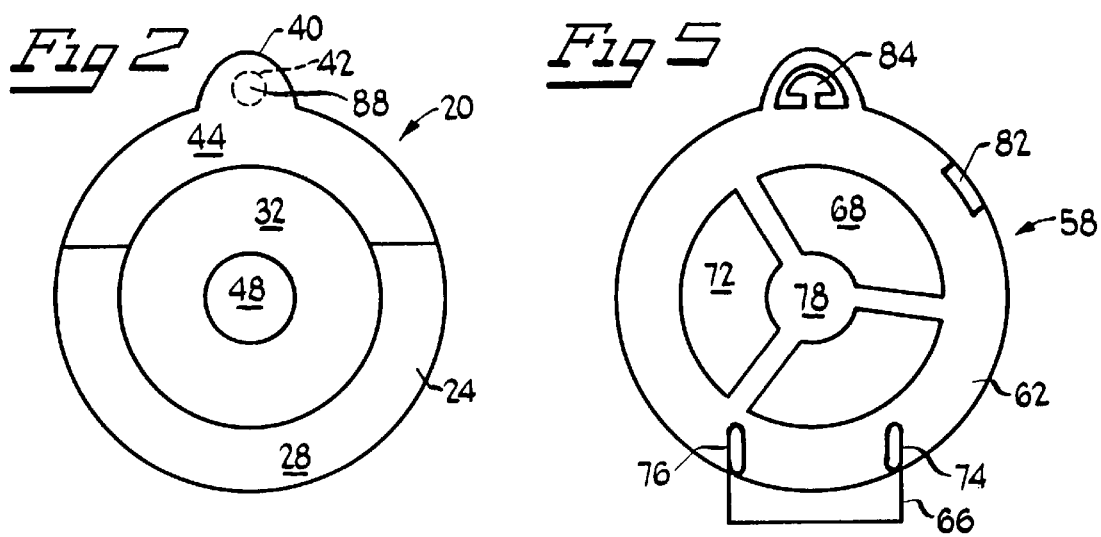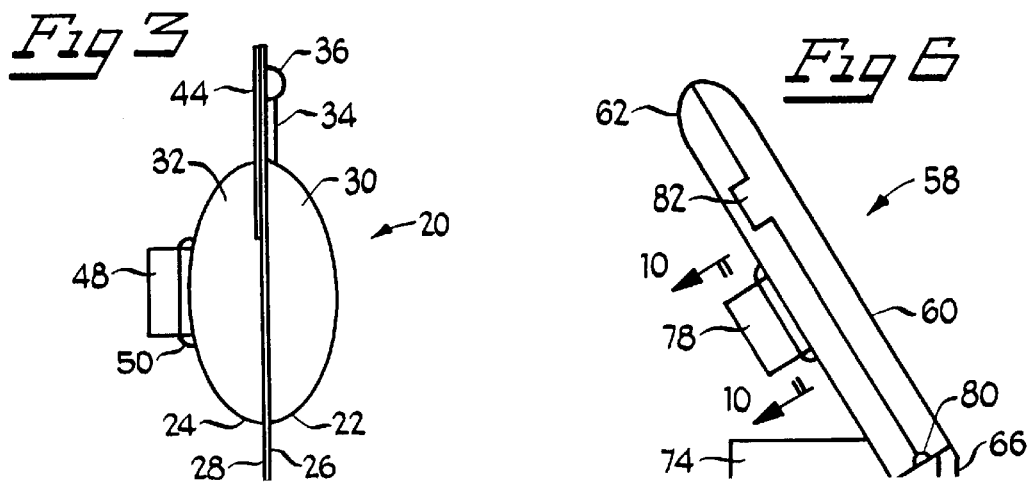

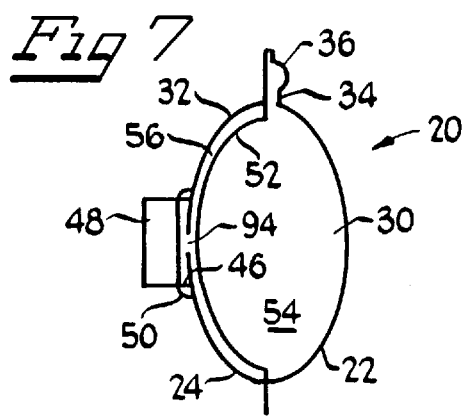
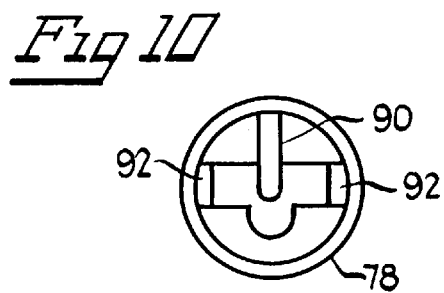
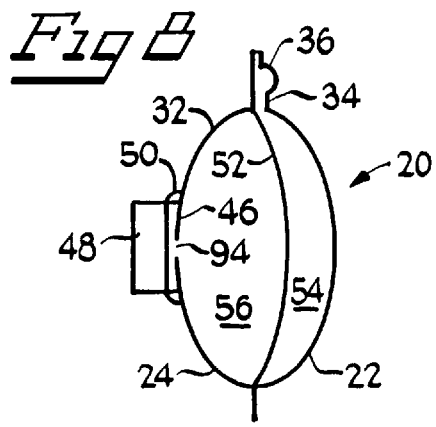
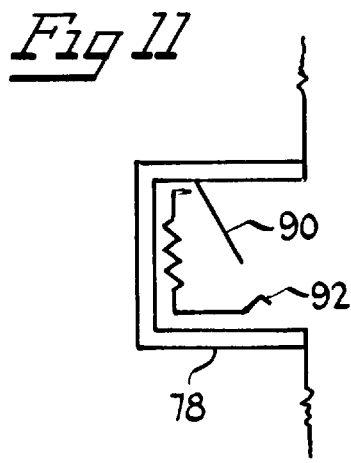
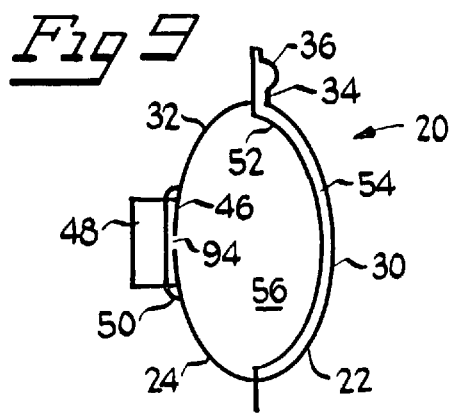
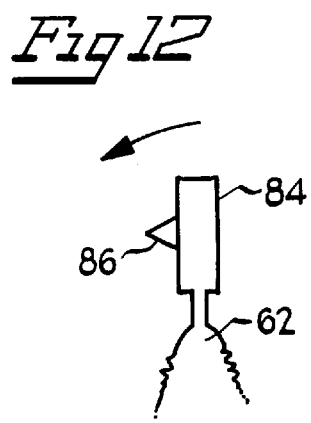

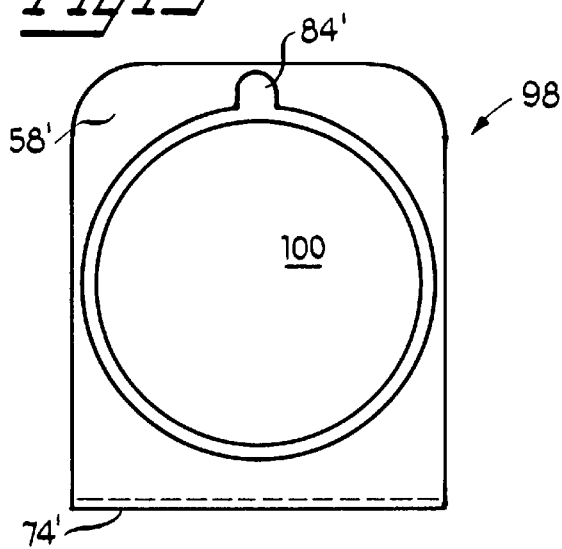
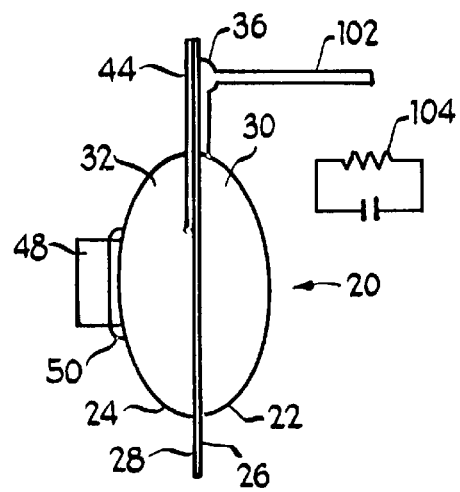
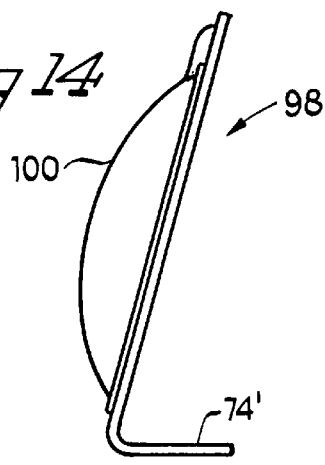
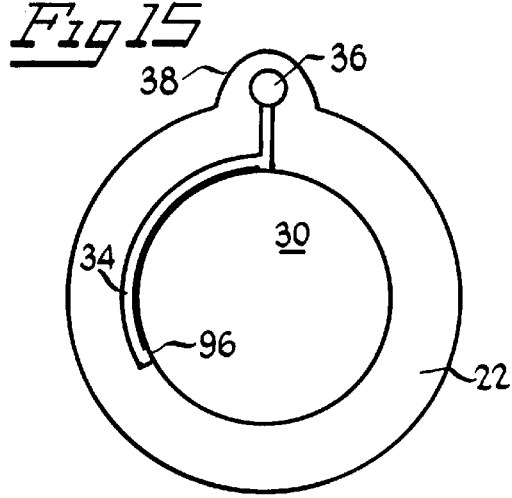
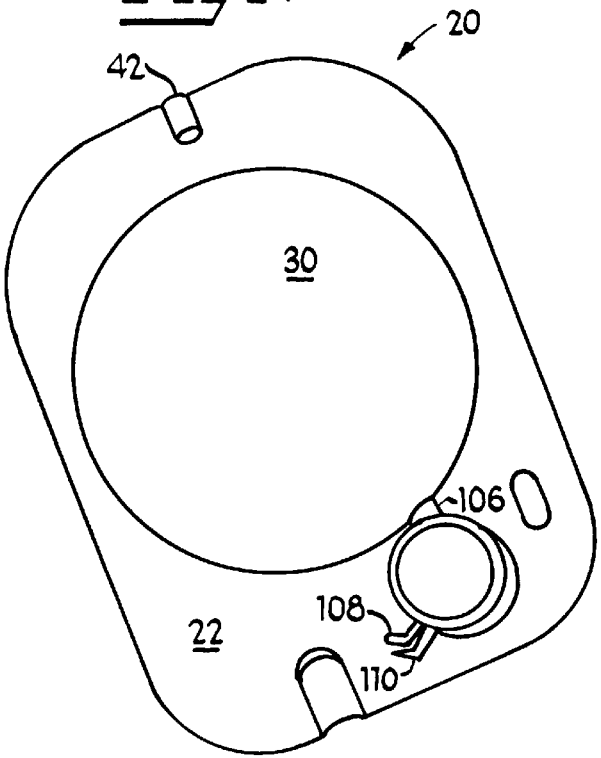

ELECTROCHEMICAL DEVICE FOR DELIVERY OF VOLATILE SUBSTANCES

TECHNICAL FIELD

The invention generally relates to methods and associated apparatus for controllably delivering volatile substances, and specifically to methods and apparatus for the controlled delivery of a volatile substance such as an air freshener or insect repellant by the use of an electrochemical gas generating cell pump.

BACKGROUND

Various methods have been used to mask or "freshen" the air in an enclosed environment (e.g. a room or automobile). For freshening the air in a room, methods used have included burning scented candles or incense or using electrical devices such as that disclosed in U.S. Pat. No. 4,849,606 to Martens et al. (Jul. 18, 1989). Martens et al. discloses a tamper resistant container used to hold a volatile material for slow diffusion. U.S. Pat. No. 5,373,581 to Smith et al. (Dec. 13, 1994) discloses a device somewhat similar to that of Marens et al. for use in an automobile.

Another fragrance emitting system for use in automobiles is disclosed in U.S. Pat. No. 5,171,485 to Ryan (Dec. 15, 1992). The Ryan device consists of a plastic reservoir which houses liquid fragrance, and a pump that extracts the fragrance from the reservoir and transports it to a holder mounted in an air vent. While fine for certain applications, the device is not integrated into a single unit, and evidently relies on an external power source to power the pump.

DISCLOSURE OF THE INVENTION

The invention includes an electrically controlled pump for dispersing a volatile substance into a local environment. The pump includes an enclosure defining a volume, a moveable member separating the enclosure into first and second chambers (the second chamber containing a vaporizable non-solid containing the volatile substance), and an electrochemical cell for generating gas. The electrochemical cell is associated with the enclosure, and is in fluid communication with the first chamber. A port communicates the second chamber with a surface or medium (e.g. gauze or a sponge) for dispersing the volatile substance into the local environment.

The invention also includes a case for encasing the pump and holding it in an upright position with respect to a surface upon which the case is positioned. The case generally includes a hinged, vented enclosure, and—positioned for interacting with the electrochemical cell—electrical circuitry for actuating the electrochemical cell.

The case will generally maintain the pump in a generally perpendicular position (±45°) with respect to the surface upon which the case is positioned. :1 will also preferably maintain the port in a position generally distal to the surface upon which the case is positioned (e.g. in a "12 o'clock" position but generally within 30° of 12 o'clock in one embodiment). The case preferably includes some means for actuating the cell and pump.

In a particular embodiment, the case and pump are integrally formed.

BRIEF DESCRIPTION OF THE FIGURES

In the drawings, which depict presently preferred embodiments of the invention and in which like reference numerals refer to like parts:

FIG. 1 depicts a front view of a cartridge for use according to the present invention.

FIG. 2 depicts a back view of the cartridge of the preceding figure.

FIG. 3 depicts a side view of the cartridge of the preceding two figures.

FIG. 4 depicts a front view of a case for use with the cartridge of the preceding three figures.

FIG. 5 depicts a back view of the case of the preceding figure.

FIG. 6 depicts a side view of the case of the preceding two figures.

FIG. 7 depicts a sectional view of the cartridge of FIGS. 1 through 3 wherein the reservoir compartment is full of liquid.

FIG. 8 depicts a sectional view of the cartridge of FIGS. 1 through 3 wherein the reservoir compartment has been partially emptied of liquid.

FIG. 9 depicts a sectional view of the cartridge of FIGS. 1 through 3 wherein the reservoir compartment is empty of liquid.

FIG. 10 depicts a sectional view of a portion of the case taken along section line 10—10 of FIG. 6.

FIG. 11 depicts a stylized cut-away side-view of the case portion of the preceding figure.

FIG. 12 depicts an enlarged, stylized side-view of a "switch" for actuating a device according to the present invention.

FIG. 13 depicts a side view of an integrated device according to the invention.

FIG. 14 depicts a front view of the device according to the preceding figure.

FIG. 15 depicts a front view of an alternative embodiment of a cartridge for use in the present invention.

FIG. 16 conceptionally depicts a side view of a cartridge associated with a heating element for volatilizing the fluid.

FIG. 17 is a perspective view of an alternative device for delivering a volatile substance.

BEST MODE OF THE INVENTION

As depicted in FIGS. 1 through 3, a cartridge or pump, generally 20, includes front and back bowl-shaped shell members or halves 22, 24 which are associated with one another about their respective flat, outer rings 26, 28. These rims 26, 28 circumferentially define bowl-shaped portions 30, 32 of the shells 22, 24. The shells 22, 24 are preferably rigid members, preferably made of a material such as polypropylene, BAREX™ 210 or 218, poly(vinylidene chloride) ("PVDC"), polyethyltriacetate ("PETA"), poly (ethylene terephthalate) ("PET"), high density polyethylene ("EHDPEBE"), or mixtures thereof. The thickness of the shells will typically range from about 0.005 inches to about 0.1 inch. The bowl-shaped portions will (together) preferably define a fixed volume of from about 0.5 cc to about five (5) liters.

The front shell 22 (FIG. 1) has a channel 34 formed in a portion of its otherwise flat outer rim 26. This channel 34 runs from the cavity of the bowl 30 to a smaller nodule 36 formed in the rim 26. As more thoroughly described hereinafter, this nodule 36 serves as a receptacle for a liquid or runny gel including a volatile substance which is contained within a reservoir partially enclosed by the bowl 30. The nodule 36 and the channel 34 co-operate with one another as a "port" to communicate material contained within the second chamber to the outside environment, and are together formed into a lobe 38 of the flat outer rim 26.

The back shell 24 has an outer perimeter (FIG. 2) and inner perimeter of the flat outer rim generally corresponding in size and shape to the outer perimeter of the front shell 22 and inner perimeter of the flat outer shell 26 respectively. The back shell 22 also has a lobe 40 corresponding to the lobe 38 of the front shell 22. In this lobe 40, an aperture 42 is formed. This aperture is placed so as to correspond with the nodule 36 of the front shell 22 when the two shells 22, 24 are associated with one another as hereinafter described. On the upper portion of the back shell 24 is adhered gauze, cotton, cloth, paper, tissue, felt, sponge, or other liquid absorbent material 44. This liquid absorbent material serves as a medium for evaporation of the liquid pumped thereon to disperse the volatile substance into the local atmosphere. The material will typically have a high surface to volume ratio.

In an alternative embodiment (FIG. 16), the device is coupled to a small heated surface rather than the previously described medium, thus allowing a broader range of fluids to be volatilized. In such an embodiment, the fluid to be aromatized is directed via a conduit 102 from the cartridge 20 to a surface such as a small heating element 104 (e.g. a chip resistor). The heating element may be powered by electrical circuitry associated with a battery or other power source or other may be heated by other heating means. The material contained within the pump comes into contact with the heated surface 104, and volatilizes. Such an embodiment is especially useful for aromatizing certain insecticides and other liquids having a higher boiling point.

As shown in FIGS. 7–9, formed in the back shell 24 is preferably a moisture impermeable, gas permeable well 46 sized to accommodate a portion of an electrochemical cell 48. This well may have apertures or vents formed therein. A glass or silicone bead 50 may be used to seal the electrochemical cell 48 to the back shell 24. Cyanoacrylate adhesive may also be used for this purpose.

Electrochemical cells capable of generating gases such as oxygen ($O_2$), hydrogen, nitrogen, halogen (e.g. $Cl_2$, bromine, iodine), carbon dioxide, and mixtures thereof are known. See, e., U. S. Pat. No. 4,402,817 and 4,522,698 to Maget (Jun. 11, 1985) which describe electrochemical cells. Preferred electrochemical cells for use with the invention include metal electrolyte electrochemical cells capable of generating hydrogen. Electrochemical cells include solid polymer electrolyte-based oxygen or hydrogen generators, zinc type hydrogen gas generating cells (see, e.g., U.S. Pat. No. 5,245,565 to Winsel (Sep. 7, 1993) or U.S. Pat. No. 4,023,648 to Orlitzky et al.), $Cu(OH)_2$ or carbonate-based oxygen generating cells, NaSiCON-based $CO_2/O_2$ generating cells (see, International Application No. PCT/US96/04359 (International Publication No. WO 96/30563, published Oct. 3, 1996) to Ceramatec, Inc. (corresponding to co-owned, co-pending U.S. patent application Ser. No. 08/413,635 filed on Mar. 30, 1995, now U.S. Pat. No. 5,593,552), or nitrogen generating batteries see, e.g., U.S. Pat. No. 5,427,870 (Jun. 27, 1995)). The contents of all of these referenced patents and patent application are incorporated by this reference. Some cells require separate power sources (e.g. a battery), while others are self-powered.

As described in U.S. Pat. No. 4,902,278, a voltage gradient established across the electrochemical cell ionizes an electrochemically active material (e.g. atmospheric oxygen) at an electrode, transporting the ions through an electrolytic membrane to the other electrode, and reconverts the ions to molecules of the electrochemically active material which is evolved at the second electrode. In a presently preferred embodiment, a resistor, thermistor or combination thereof is placed between the cells' electrodes (not shown).

As shown in FIG. 3, the front and back shells 22, 24 are associated with one another in clam shell fashion. As is shown in FIGS. 7 through 9 (and as more thoroughly described herein), sandwiched between the two shells 22, 24 is a flexible, movable membrane 52. The membrane 52 is sized to cover the opening of the entire "bowl section" 30, 32 of the two shells 22, 24 so as to form two chambers 54, 56. The membrane 52 prevents fluid communication between the two chambers 54, 56. The membrane also extends up over the lobes 38, 40 of the shells 22, 24 including the channel 34 and associated opening of the nodule 36 in the front shell, thus closing the aperture 42 formed in the back shell 24 from communication with the outside atmosphere.

Instead of the "clam shell" design depicted in FIGS. 1–3 and 7–9, a cylindrical member could alternatively be used as an enclosure for the cartridge. In that case, instead of using a flexible membrane as the movable member separating the driving chamber and non-solid reservoir chamber, an alternative structure such as a piston placed within the cylinder could be used. In that case, the piston would preferably have means such as rings or seal for fluidically separating the two chambers.

A movable member such as flexible membrane 52 can be formed of materials which are more or less impermeable to the gas produced by the cell, and impermeable to any liquid contained within the front chamber 54. Such materials generally include films such as metaled, partially metallized or non-metallized PETA, PET, PVDC, BAREX™ 210 or 218, metallized or partially metallized polypropylene, metallized or partially metallized polyethylene glycol, or mixtures thereof.

Preferably, the moveable member has a gas permeability (with respect to the particular gas or gases produced by the electrochemical cell, such as hydrogen) less than that of the gas permeability of the material of the enclosure to the gas so that the generated gas will preferentially leak out of the device 20 before leaking across the moveable member (e.g. membrane 52). In one embodiment, the gas permeability of the enclosure 32 is so great that small amounts of gas will leak from the electrochemical cell during storage, and will pass through the enclosure 32, but volatile substance contained within the second chamber will not leak therefrom. In another embodiment (see, e.g., FIG. 15), any gas that might pass through the membrane into the second chamber rises to the top of the device, while the entry port to the channel 34 is placed lower in the structure gas never substantially exits through the port until all of the fluid has been dispensed. In such ways, the device exhibits generally linear delivery ("linear performance" over time) of the fluid.

A preferred housing or case, generally 58, for containing the cartridge or pump 20 is depicted in FIGS. 4–6. The depicted case, like the cartridge, has a front shell 60 and back shell 62. The case is generally sized and shaped to accept or encase an appropriately sized cartridge.

The front case shell 60 has an aperture 64 or apertures to allow a gas (e.g. the vaporized volatile substance such as a scented oil) to pass therethrough FIG. 4). In the depicted embodiment, the bowl 30 of an encased cartridge could protrude therethrough (not shown). The aperture may be replaced with or covered by a plurality of apertures, a grate, screen or similar structure (not shown). In the depicted embodiment, the front case shell 60 is associated with a frame or foot 66 for assisting in keeping the case 58 and any encased cartridge upright.

As shown in FIG. 5, the back case shell 62 also has apertures 68, 70, 72 to allow gas to pass therethrough. Such apertures too may be modified as previously described with regard to the front shell case. In the depicted embodiment, feet 74, 76 are associated with the back case shell 62 which assist in keeping the case 58 and any encased cartridge in an upright position. The back case shell 62 also has a housing portion 78 for containing the electrochemical cell 48. This housing portion 78 may also contain electrical circuitry which is hereinafter described with respect to FIGS. 10 & 11. Alternatively, this electrical circuitry can contain components, such as an integrated chip or timer (not shown), to purse the cell and thus have the pump put out liquid only at selected time intervals so as to prolong the life of the cartridge.

The back and front case shells 60, 62 are associated together in a clam shell-type arrangement with, for example, a hinge 80 (FIG. 6). The shells 60, 62 pivot about the hinge and may fixedly interact with one another by use of, for example a latch or clasp 82. In such a manner, a cartridge may be placed within "open" hinged shell halves 60, 62, and the case then shut to contain the cartridge. An actuation switch or press tab 84 is shown associated with the back shell half corresponding to the lobe 38, 40 of a cartridge 20 which may be used as described herein.

In use, the front chamber 54 of the cartridge 20 is preferably pre-filled with a volatile substance, such as an aromatic oil dissolved in a solvent such as ethanol (FIG. 7). The thus filled cartridge is inserted into the back shell half 62 so that the lobe 38, 40 fits within the portion of the back shell designed to accept it (that portion associated with press tab 84 generally) and so that electrochemical cell 48 interacts with electrodes 90, 92 positioned within the cell housing 78. The cell housing may have apertures formed therein. Such placement completes an electrical circuit with the electrochemical cell 48, causing it to generate gas. The case 58 is then closed and the clasp 82 associated with the front shell half 60 interacts with the back shell half 62 and retains the two halves 60, 62 together encasing the cartridge 20.

The press tab 84 is then pressed, and the membrane 88 covering the nodule 36 is punctured. As shown in FIG. 12, the press tab 84 has a pointed member 86 which punctures the membrane portion 88 closing the aperture 42 of the back cartridge shell 24, thus exposing the nodule 36 in the front cartridge cell 22 to the outside atmosphere.

Gas generated by the electrochemical cell 48 passes through the well 46 in the outer shell bowl 32 through, for example an aperture 94 formed therein. The gas entering the back chamber 56 causes the back chamber to increase in volume, thus moving flexible membrane 52 and decreasing the size of the front chamber 54 (FIG. 8). This decrease in size in the front chamber 54 drives liquid contained within it to pass upwards through the channel 34 and go to the nodule 36. The liquid or gel pours out through the hole formed in the membrane portion 88 covering the nodule and pours out onto the evaporative pad 44. The volatile portion of the composition evaporates and passes out the various apertures 64, 68, 70, 72 and any volatile substance contained therein (e.g. air freshener, scent, insect repellant, etc.) also evaporates and disperses into the surrounding atmosphere. As shown in FIG. 9, the front chamber 54 eventually empties, and, if desired, the cartridge can be replaced.

A "stand alone" version of the device integrates both the cartridge and the case 58' into a single structure. Such an embodiment, generally 98, is depicted in FIGS. 13 & 14. In the depicted embodiment, the electrochemical cell and the pump are housed completely within the structure 98. A stand 74' or similar structure is used to keep the device in a generally upright position (90°±30°) with respect to a horizontal surface upon which the device would be placed. The fluid reservoir is contained within a bulbous portion 100. A switch, press tab 84' or other means for actuating the device is placed proximate the disbursing medium. In other regards, the integrated device 98 works similarly to the previously described devices.

In one embodiment, the opening to the channel is placed at an approximate 6 o'clock position in the device so that if a gas bubble should form in the volatile fluid containing chamber (e.g. by hydrogen permeation through the membrane separating the chambers), the bubble will push an amount of fluid equal volume from the chamber. Thus, the rate of fluid delivery remains proportional to the rate of gas generated by the cell. For instance, in the embodiment depicted in FIG. 15, the opening 96 to the channel 34 is placed at 8 o'clock. In such an embodiment, the channel 34 preferably lays around the rim 26 of the device going to the lobe 38 and associated medium for dispersing the fluid into the atmosphere. Such placement reduces structural interference with the housing 58.

The device 20 depicted in FIG. 17 can be used either as a "stand alone" version or as a cartridge to be associated with a case. This device too has an electrochemical cell 48 in fluid communication via a conduit with the first chamber. The port or aperture 42 is placed in a general "12 o'clock" position with respect to the structure. Two wires or leads 108, 110 are in electrical connection with the electrochemical cell 48. Interconnection of the two wires 108, 110 actuates the cell 48, and the device operates as previously described with respect to the other devices of the invention.

Various alternatives in the invention will become readily apparent to those of skill in the art. For instance, the electrochemical cell may be contained within a chamber or may be connected by conduit to the chamber. Instead of ethanol, other lower alcohols such as isopropanol or methanol can be used as can other organic and non-organic solvents for the volatile substance. Scented oils such as cinnamon oil and clove oil can be used.

A relatively smaller version of the device can be used to disperse flea and tick repellant about a dog, cat or other animal. Larger devices can be used with herd animals, such as cows, to dispense pest repellents about the animal. E such an embodiment, the foot or other stand could be replaced with a clip, staple, belt, or other equivalent means to attach the device to the animal. A suitable pesticide or pest repellant could then be contained within the reservoir to dispense over time about the animal. Since the device drives the fluid out of the reservoir, problems associated with prior art devices (such as flea collar) due to environmental conditions could be avoided (e.g. soil would not clot the device sufficiently to prevent the volatile fluid from being dispensed).

Although the invention has been described with regard to certain preferred embodiments, the scope of the invention is to be defined by the appended claims.

What is claimed is:

1. A method of dispersing a volatile substance into a local environment from an enclosure having a volume and first and second chambers, said first and second chambers sealedly divided by a displacement member fixed therebetween, said displacement member flexible within said enclosure, said second chamber containing a non-solid composition comprising the volatile substance, said method comprising:

electrochemically generating gas into the first chamber thus moving the displacement member, compressing the second chamber, and displacing said non-sold composition out of said second chamber via an outlet in fluid communication with the local environment associated with said second chamber, thus dispersing the volatile substance into the local environment.

2. An apparatus for dispersing a volatile substance into a local environment, said apparatus comprising:

an enclosure having an exterior wall, said exterior wall having a permeability to a gas and further defining a volume;

a moveable member separating said enclosure into a first chamber and a second chamber, said moveable member also having a permeability to said gas, the gas permeability of said moveable member being less than the gas permeability of the exterior wall, said second chamber further containing a non-solid composition comprising a volatile substance;

an electrochemical cell for generating said gas associated with said enclosure, and in fluid communication with said first chamber; and a port communicating said second chamber with a medium for dispersing the non-solid composition so as to allow the volatile substance to disperse into the local environment.

3. The apparatus of claim 2 wherein said enclosure comprises two shell halves sized and shaped to integrate with one another, and the moveable member is a flexible membrane sandwiched therebetween.

4. The apparatus of claim 3 wherein the flexible membrane has a hydrogen gas permeability less than that of the enclosure.

5. The apparatus of claim 2 wherein said medium for dispersing the non-solid composition is a piece of cloth adhered to said enclosure adjacent to said port.

6. A case for encasing the apparatus of claim 5 and holding the apparatus in a generally upright position with respect to a surface upon which the case is positioned, said case comprising:

an encasement member capable of being opened and closed, said encasement member containing a vent;

electrical circuitry for actuating said electrochemical cell associated with said encasement member, said electrical circuitry positioned to interact with said electrochemical cell; and means for puncturing the membrane covering the port of the second chamber of the apparatus.

7. The apparatus of claim 2 wherein said electrochemical cell is a metal electrolyte electrochemical cell.

8. The apparatus of claim 7 wherein the electrochemical cell generates hydrogen gas.

9. The apparatus of claim 8 wherein the enclosure of the second chamber is permeable to hydrogen gas, such that a bubble of the gas does not form within the second chamber.

10. The apparatus of claim 2 wherein a gas diffusing through the moveable member from the first chamber to the second chamber does not pass out of the port until the non-solid composition has been entirely expelled out of said second chamber.

11. The apparatus of claim 2 wherein a gas diffusing through the moveable member from the first chamber to the second chamber passes out of the port.

12. A case for encasing the apparatus of claim 2 and holding the apparatus in a generally upright position with respect to a surface upon which the case is positioned, said case comprising:

an encasement member capable of being opened and closed, said encasement member containing a vent; and electrical circuitry for actuating said electrochemical cell associated with said encasement member, said electrical circuitry positioned to interact with said electrochemical cell.

13. The case of claim 12 wherein the case maintains the port associated with said second chamber of said apparatus in a position distal to the surface upon which the case is positioned.

14. The case of claim 13 wherein said case maintains said apparatus in a generally perpendicular position with regard to the surface upon which the case is positioned.

15. The case of claim 14 wherein the case further comprises actuation means for actuating the electrochemical cell of the apparatus.

16. The apparatus of claim 2 further comprising a liquid-tight membrane covering said port.

17. The apparatus of claim 2 wherein the enclosure is rigid and defines a fixed volume.

18. The apparatus of claims 2 wherein the medium for dispersing the non-solid composition is a heated surface.

19. The apparatus of claim 2 wherein said electrochemical cell is a copper hydroxide-based, oxygen generating electrochemical cell.

20. The apparatus of claim 2 wherein said gas comprises hydrogen or carbon dioxide.

21. An apparatus for vaporizing a volatile substance comprising:

a generally upright enclosure defining a fixed volume, and further having a port associated therewith, said port being located at from about 12 o'clock to about 10 o'clock in said enclosure;

a moveable member separating said enclosure into a first chamber and a second chamber within said fixed volume, said second chamber containing a non-solid composition comprising a volatile substance, said second chamber being in fluid communication with said port; and an electrochemical cell for generating a gas, said electrochemical cell in fluid communication with said first chamber and moveable member, whereby, when said electrochemical cell generates gas, said first chamber expands, and said second chamber contracts displacing said non-solid composition from said second chamber for vaporization.

22. The apparatus of claim 21 wherein said moveable member is a flexible membrane.

23. The apparatus of claim 22 wherein said enclosure comprises two shell halves sized and shaped to integrate with one another, and the moveable member is a flexible membrane sandwiched therebetween.

24. An apparatus for vaporizing a volatile substance comprising:

a generally upright enclosure defining a fixed volume, and further having a port associated therewith, said port being located at from about 4 o'clock to about 8 o'clock, travelling clockwise, in said enclosure;

a moveable member separating said enclosure into a first chamber and a second chamber within said fixed volume, said second chamber containing a non-solid composition comprising a volatile substance, said second chamber being in fluid communication with said port; and an electrochemical cell for generating a gas, said electrochemical cell in fluid communication with said first chamber and moveable member, whereby, when said electrochemical cell generates gas, said first chamber expands, and said second chamber contracts displacing said non-solid composition from said second chamber for vaporization.

* * * * *

UNITED STATES PATENT AND TRADEMARK OFFICE
CERTIFICATE OF CORRECTION

PATENT NO. : 5,899,381
DATED : May 4, 1999
INVENTOR(S) : Gordon, et. al.

It is certified that error appears in the above-identified patent and that said Letters Patent is hereby corrected as shown below:

Col. 5, line 11 — Delete "purse" and insert instead -- pulse --.

Col. 6, line 43 — Delete "E" and insert instead -- In --.

Col. 7, line 1 — Delete "non-sold" and insert instead -- non-solid --.

Signed and Sealed this

Eleventh Day of January, 2000

Attest:

Q. TODD DICKINSON

*Attesting Officer*  *Acting Commissioner of Patents and Trademarks*